US007495072B2

(12) United States Patent
Dolitzky

(10) Patent No.: US 7,495,072 B2
(45) Date of Patent: Feb. 24, 2009

(54) PROCESS FOR PREPARATION OF MIXTURES OF POLYPEPTIDES USING PURIFIED HYDROBROMIC ACID

(75) Inventor: Ben-Zion Dolitzky, Petach-Tikva (IL)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 0 days.

(21) Appl. No.: 11/223,072

(22) Filed: Sep. 9, 2005

(65) Prior Publication Data
US 2006/0052586 A1   Mar. 9, 2006

Related U.S. Application Data

(60) Provisional application No. 60/608,843, filed on Sep. 9, 2004.

(51) Int. Cl.
C07K 1/00 (2006.01)
C07K 1/06 (2006.01)
C07K 1/14 (2006.01)
(52) U.S. Cl. .................. 530/333; 530/335; 530/336; 530/337; 530/344
(58) Field of Classification Search .................. None
See application file for complete search history.

(56) References Cited

U.S. PATENT DOCUMENTS

| | | | |
|---|---|---|---|
| 3,846,550 A | | 11/1974 | Teitelbaum et al. |
| 3,849,550 A | * | 11/1974 | Teitelbaum et al. ...... 424/78.29 |
| 4,264,499 A | * | 4/1981 | Hirai et al. .................. 540/563 |
| 4,594,409 A | | 6/1986 | Hayashi et al. |
| H1312 H | * | 5/1994 | Coughlin et al. ............ 530/331 |
| 5,800,808 A | * | 9/1998 | Konfino et al. ........... 424/78.08 |
| 5,858,964 A | | 1/1999 | Aharoni et al. |
| 5,872,122 A | * | 2/1999 | Bovy et al. .................. 514/256 |
| 5,981,589 A | * | 11/1999 | Konfino et al. .............. 514/561 |
| 6,048,898 A | | 4/2000 | Konfino et al. |
| 6,054,430 A | | 4/2000 | Konfino et al. |
| 6,214,791 B1 | | 4/2001 | Arnon et al. |
| 6,342,476 B1 | | 1/2002 | Konfino et al. |
| 6,362,161 B1 | | 3/2002 | Konfino et al. |
| 6,514,938 B1 | | 2/2003 | Gad et al. |
| 6,620,847 B2 | | 9/2003 | Konfino et al. |
| 6,624,180 B2 | * | 9/2003 | South et al. .................. 514/352 |
| 6,800,285 B2 | | 10/2004 | Rodriguez |
| 6,800,287 B2 | | 10/2004 | Gad et al. |
| 6,939,539 B2 | | 9/2005 | Konfino et al. |
| 7,022,663 B2 | | 4/2006 | Gilbert et al. |
| 7,033,582 B2 | | 4/2006 | Yong et al. |
| 7,049,399 B2 | * | 5/2006 | Bejan et al. .................. 530/333 |
| 7,074,580 B2 | | 7/2006 | Gad et al. |
| 7,163,802 B2 | | 1/2007 | Gad et al. |
| 7,199,098 B2 | | 4/2007 | Konfino et al. |
| 7,279,172 B2 | | 10/2007 | Aharoni et al. |
| 2003/0170729 A1 | | 9/2003 | Klinger |
| 2004/0091956 A1 | | 5/2004 | Bejan |
| 2005/0256046 A1 | | 11/2005 | Gad et al. |
| 2006/0122113 A1 | * | 6/2006 | Pinchasi et al. ............... 514/12 |
| 2006/0172942 A1 | | 8/2006 | Dolitzky |
| 2007/0021324 A1 | * | 1/2007 | Dolitzky ........................ 514/2 |
| 2007/0021341 A1 | | 1/2007 | Sela et al. |
| 2007/0048794 A1 | | 3/2007 | Gad et al. |
| 2007/0054857 A1 | | 3/2007 | Pinchasi et al. |

FOREIGN PATENT DOCUMENTS

| | | |
|---|---|---|
| DE | 3930733 | 3/1991 |
| EP | 0378246 | 6/1990 |
| RU | 1469826 | 11/1995 |
| SU | 1182051 | 9/1985 |
| SU | 1690368 | 8/1990 |
| SU | 1664845 | 7/1991 |
| WO | 9800375 | 1/1998 |
| WO | 9916747 | 7/1999 |
| WO | 9922402 | 9/1999 |
| WO | 9927107 | 11/1999 |
| WO | 0105198 | 2/2001 |
| WO | 0118248 | 6/2001 |
| WO | 0119649 | 6/2001 |
| WO | 02038859 | 12/2002 |
| WO | 03001744 | 11/2003 |
| WO | 2004036172 | 10/2004 |
| WO | 2005039003 | 10/2005 |
| WO | 2007072865 | 7/2007 |

OTHER PUBLICATIONS

33% Hydrobromic acid in acetic acid product sheet BC0036 (Aug. 1999), 2 pages.*
MSDS Hydrobromic acid 33-35%, in Acetic Acid. ACC#00739; Acros Organics N.V., created Jul. 22, 1999, revision #3 Mar. 18, 2003.* HunterLab "Insight on Color: APHA Q & A" (2003) 15(5) (Rev Feb. 2005), 4 pages.*
HunterLab "Insight on Color: APHA" (1996) 8(16) (Rev May 2005), 3 pages.*
U.S. Appl. No. 11/502,787, filed Aug. 10, 2006, Gad et al.
U.S. Appl. No. 11/373,794, filed Mar. 9, 2006, Pinchasi et al.
Aharoni, R., "Copolymer 1 inhibits manifestations of graft rejection," Transplantation, Aug. 2001, 72(4), 598-605.
Bodanszky, M., "Principles of Peptide Synthesis," Springer-Verlag, Berlin, Heidelberg, New York, Tokyo, 1984, 118-229.
Bornstein, Hosp. Pract. (Off. Ed.), May 15, 1992, vol. 27 (No. 5) L135-138, 141-142, 145-158.
Bornstein, "Cop 1 May be Beneficial for Patients with Exacerbating-remitting Form of Multiple Sclerosis", Adv. Ther. (USA), 1987, 4, 206 (Abstract).
Bornstein, et al., "A Pilot Trial of Cop 1 in Exacerbating-remitting Multiple Sclerosis", New Eng. J. Med., 1987, 317(7), 408-414.
Bornstein, et al., "A Placebo-controlled, Double-blind, Randomized Two-center, Pilot Trial of Cop 1 in Chronic Progressive Multiple Sclerosis", Neurol., 1991, 41, 533-539.

(Continued)

Primary Examiner—Andrew D Kosar
(74) Attorney, Agent, or Firm—John P. White; Cooper & Dunham LLP

(57) ABSTRACT

The subject invention provides an improved process for obtaining a mixture of polypeptides having nonuniform amino acid sequences, where each polypeptide consists essentially of alanine, glutamic acid, tyrosine and lysine where the resulting mixture of polypeptides comprises less than 0.3% brominated tyrosine and less than 1000 ppm metal ion impurities.

21 Claims, No Drawings

OTHER PUBLICATIONS

Bornstein, et al., "Clinical Experience with COP-1 in Multiple Sclerosis", *Neurology*, 1988 38 (Suppl. 2) 66-69.

Bornstein, et al., "Rationale for Immunomodulating Therapies of Multiple Sclerosis", *Neurology*, 1988 38 (Suppl. 2) 80-81.

Bornstein, et al., "Clinical Trials of a Synthetic Polypeptide (Copolymer 1) for the Treatment of Multiple Sclerosis" in Gonsett et al., *Immunological and Clinical Aspects of Multiple Sclerosis* (MTP Press, The Hague, 1984) 144-150.

Bornstein, et al., "Clinical Trials of Cop 1 in Multiple Sclerosis" in *Handbook of Multiple Sclerosis* (S.D. Cook Marcel Rekker, ed., 1990) 469-480.

Bornstein, et al., "Clinical Trials of Copolymer 1 in Multiple Sclerosis", *Ann. N.Y. Acad. Sci.* (USA), 1984, 366-372.

Bornstein, et al., "Multiple Sclerosis: Clinical Trials of a Synthetic Polypeptide, Copolymer 1", *Neurol.*, 1985, 35 (Suppl. 1), 103 (Abstract).

Bornstein, et al., "Multiple Sclerosis: Trial of a Synthetic Polypeptide", *Ann. Neurol.*, 1982, 11, 317-319.

Bornstein, et al., "Pilot Trial of COP-1 in Chronic Progressive Multiple Sclerosis: Preliminary Report", from *The International Multiple Sclerosis Conference: An Update on Multiple Sclerosis*, Roma (Italy), Sep. 15-17, 1988, in Elsevier Science Publisher, 1989, 225-232.

Bornstein, et al., "Treatment of Multiple Sclerosis with a Synthetic Polypeptide: Preliminary Results", *Ann. Neurol.*, 1980, 8, 117 (Abstract).

Bornstein, et al., "Treatment of Multiple Sclerosis with a Synthetic Polypeptide: Preliminary Results", *Trans. Am. Neurol. Assoc.*, 1980, 105, 348-350.

Bornstein, et al, "Treatment of Multiple Sclerosis with Copolymer 1" in *Treatment of Multiple Sclerosis: Trial, Design, Reults and Future Perspectives* (Rudick R.A. & Goodkin D.E., eds., Springer Verlag, London, 1992) 173-198.

Korczyn et al., "Safety profile of copolymer 1: Analysis of cumulative experience in the United States and Israel," *J. Neurol.*, Apr. 1996; 243 (4 Suppl 1) pp. S23-S26; and.

Teitelbaum D., Copolymer 1 induces T cells of the T helpe type 2 that crossreact with myelin basic protein and suppress experimental autoimmune encephalomyelitis, *Proc. Natl. Acad. Sci. U.S.A.*, Sep. 1997, 94(20), 10821-10826.

U.S. Appl. No. 10/577,588, filed Oct. 28, 2004, Rosenberger et al.

U.S. Appl. No. 12/074,106, filed Dec. 22, 2008, Pinchasi.

"COPAXONE®" in Physician's Desk Reference, Medical Economics Co., Inc., Montvale, NJ, 2003, 3214-3218.

Copaxone® (glatiramer acetate injection), prescribing information, http://www.copaxone.com/pdf/PrescribingInformation.pdf.

PCT Written Opinion issued Oct. 9, 2007 for International Application No. PCT/US05/32395.

PCT International Search Report issued Oct. 9, 2007 for International Application No. PCT/US05/32395.

PCT International Preliminary Report on Patentability issued Oct. 30, 2007 for International Application No. PCT/US05/32395.

\* cited by examiner

PROCESS FOR PREPARATION OF MIXTURES OF POLYPEPTIDES USING PURIFIED HYDROBROMIC ACID

This application claims benefit of U.S. Provisional Application No. 60/608,843, filed Sep. 9, 2004, the contents of which are hereby incorporated herein by reference.

Throughout this application various publications are referenced by their full citations. The disclosures of these publications in their entireties are hereby incorporated by reference into this application in order to more fully describe the state of the art to which this invention pertains.

BACKGROUND OF THE INVENTION

A mixture of polypeptides which do not all have the same amino acid sequence referred to as glatiramer acetate (GA) is marketed under the tradename COPAXONE® and comprises the acetate salts of polypeptides containing L-glutamic acid, L-alanine, L-tyrosine and L-lysine at average molar fractions of 0.141, 0.427, 0.095 and 0.338, respectively. The average molecular weight of COPAXONE® is between 4,700 and 11,000 daltons. ("COPAXONE", Physician's Desk Reference, (2000), Medical Economics Co., Inc., (Montvale, NJ), 3115.) Chemically, glatiramer acetate is designated L-glutamic acid polymer with L-alanine, L-lysine, L-tyrosine, acetate (salt). Its structural formula is:

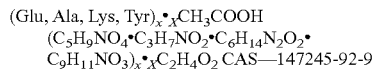

(Glu, Ala, Lys, Tyr)$_x$·$_x$CH$_3$COOH
(C$_5$H$_9$NO$_4$·C$_3$H$_7$NO$_2$·C$_6$H$_{14}$N$_2$O$_2$·
C$_9$H$_{11}$NO$_3$)$_x$·$_x$C$_2$H$_4$O$_2$ CAS—147245-92-9

("Copaxone", Physician's Desk Reference, (2000), Medical Economics Co., Inc., (Montvale, N.J.), 3115.)

Glatiramer acetate is approved for reduction of the frequency of relapses in patients with relapsing-remitting multiple sclerosis. Multiple sclerosis has been classified as an autoimmune disease. Glatiramer acetate has also been disclosed for use in the treatment of other autoimmune diseases (Publication No. U.S. 2002/0055466 A1 for R. Aharoni et al.), inflammatory non-autoimmune diseases (Publication No. U.S. 2005/0014694 A1 for V. Wee Yong et al.; and U.S. Patent Application No. 2002/0077278 A1, published Jun. 20, 2002 (Young et al.)) and to promote nerve regeneration and/or to prevent or inhibit secondary degeneration which may follow primary nervous system injury (Publication No. U.S. 2003/0004099 A1 for M. Eisenbach-Schwartz et al.; and U.S. patent application Ser. No. 2002/0037848 A1, published Mar. 28, 2002 (Eisenbach-Schwartz)). Furthermore, glatiramer acetate has been disclosed as a treatment for immune mediated diseases (e.g., U.S. Pat. No. 6,514,938 B1, issued Feb. 4, 2003 (Gad et al.); PCT International Publication No. WO 01/60392, published Aug. 23, 2001 (Gilbert et al.); and PCT International Publication No. WO 00/27417, published May 19, 2000 (Aharoni et al.) as well as diseases associated with demyelination (PCT International Publication No. WO-1/97846, published Dec. 27, 2001 (Moses et al.).

The manufacturing process as detailed in the above patents involves reacting protected polypeptides with 33% hydrobromic acid in acetic acid. (U.S. Pat. No. 5,800,808, issued Sep. 1, 1998 to Konfino, et al.) This deprotection reaction removes the gamma benzyl protecting group from the 5-carboxylate of the glutamate residue and cleaves the polymer to smaller polypeptides to form a trifluoroacetyl polypeptide. (U.S. Pat. No. 5,800,808, issued Sep. 1, 1998 to Konfino, et al.) The time needed to obtain GA of the proper average molecular weight of between 7,000±2,000 daltons depends on the reaction temperature and the molecular weight profile of the protected glatiramer acetate. (U.S. Pat. No. 5,800,808, issued Sep. 1, 1998 to Konfino, et al.) The deprotection occurs at a temperature of between 20° C. and 28° C. (U.S. Pat. No. 5,800,808, issued Sep. 1, 1998 to Konfino, et al.). A test reaction is performed on every batch at different time periods to determine the reaction time needed at a given temperature to achieve trifluoroacetyl polypeptides of a proper molecular weight profile. (U.S. Pat. No. 5,981,589, issued Nov. 9, 1999 to Konfino, et al.) The amount of time needed for the reaction ranges, for example, between 10 and 50 hours. (U.S. Pat. No. 5,800,808, issued Sep. 1, 1998 to Konfino, et al.). In addition, U.S. Pat. Nos. 5,981,589, 6,048,898, 6,054,430, 6,342,476, 6,362,161, and 6,620,847, also relate to compositions and methods for manufacture of mixtures of polypeptides, including GA.

This invention provides an improved manufacturing process.

SUMMARY OF THE INVENTION

The subject invention provides a process for obtaining a mixture of trifluoroacetyl polypeptides which do not all have the same amino acid sequence, where each polypeptide consists essentially of alanine, glutamic acid, tyrosine and trifluoroacetyl lysine, wherein the mixture has a desired average molecular weight and wherein during the process a batch of a mixture of polypeptides, each of which consists essentially of alanine, γ-benzyl glutamate, tyrosine and trifluoroacetyl lysine is deprotected with a solution of hydrobromic acid in acetic acid, the improvement comprising use of a solution of hydrobromic acid in acetic acid, which solution comprises less than 0.5% of free bromine.

The subject invention also provides a process for obtaining a mixture of trifluoroacetyl polypeptides which do not all have the same amino acid sequence, where each polypeptide consists essentially of alanine, glutamic acid, tyrosine and trifluoroacetyl lysine, wherein the mixture has a desired average molecular weight and wherein during the process a batch of a mixture of polypeptides, each of which consists essentially of alanine, γ-benzyl glutamate, tyrosine and trifluoroacetyl lysine is deprotected with a solution of hydrobromic acid in acetic acid, the improvement comprising use of a solution of hydrobromic acid in acetic acid, which solution comprises less than 1000 ppm of metal ion impurities.

The subject invention further provides process of producing a mixture of trifluoroacetyl polypeptides which do not all have the same amino acid sequence, where each polypeptide consists essentially of alanine, glutamic acid, tyrosine and trifluoroacetyl lysine, wherein the mixture has a desired average molecular weight comprising deprotecting a mixture of polypeptides each consisting essentially of alanine, γ-benzyl glutamate, tyrosine and trifluoroacetyl lysine with a solution of hydrobromic acid in acetic acid, which solution comprises less than 0.5% of free bromine and less than 1000 ppm of metal ion impurities.

The subject invention also provides a composition comprising the trifluoroacetyl product produced by any one of the subject invention processes, and a carrier.

The subject invention further provides a mixture of trifluoroacetyl polypeptides which do not all have the same amino acid sequence, where each polypeptide consists essentially of alanine, glutamic acid, tyrosine and trifluoroacetyl lysine, wherein the mixture has a desired average molecular weight, no more than 0.1% brominated tyrosine and less than 1000 ppm metal ion impurities. The subject invention also provides a composition comprising the mixture of trifluoroacetyl polypeptides and a carrier.

The subject invention also provides process for obtaining a pharmaceutical composition containing a mixture of polypeptides which do not all have the same amino acid sequence, where each polypeptide consists essentially of alanine, glutamic acid, tyrosine and lysine, and wherein the mixture has a desired average molecular weight, which comprises a) polymerizing N-carboxyanhydrides of tyrosine, alanine, γ-benzyl glutamate and N-trifluoroacetyl lysine to form a mixture of protected polypeptides;

b) deprotecting the protected polypeptides with a solution of hydrobromic acid in acetic acid, the solution comprises less than 0.5% of free bromine and less than 1000 ppm of metal ion impurities, to form a mixture of trifluoroacetyl polypeptides;

c) reacting the a mixture of trifluoroacetyl polypeptides with aqueous piperidine to form a solution of aqueous mixture of polypeptides, each of which consists essentially of alanine, glutamic acid, tyrosine and lysine; and d) purifying the mixture of polypeptides.

The subjection invention further provides process of producing glatiramer acetate comprising the steps of:

a) polymerizing N-carboxyanhydrides of tyrosine, alanine, γ-benzyl glutamate and N-trifluoroacetyl lysine to form protected glatiramer acetate;

b) deprotecting protected glatiramer acetate with a solution of hydrobromic acid in acetic acid, the solution comprises less than 0.5% of free bromine and less than 1000 ppm of metal ion impurities, to form trifluoroacetyl glatiramer acetate;

c) reacting trifluoroacetyl glatiramer acetate with aqueous piperidine to form a solution of glatiramer acetate; and d) purifying the glatiramer acetate.

The subject invention yet further provides a method of analyzing the percentage of brominated tyrosine in a sample of glatiramer acetate comprising the steps of:

a) hydrolyzing glatiramer acetate to obtain a hydrolyzate;

b) eluting, the hydrolyzate through a chromatographic column;

c) measuring the level of bromotyrosine in the hydrolyzate;

d) preparing sample solutions of the amino acid components of glatiramer acetate and of bromotyrosine;

e) eluting the sample solutions through the column of step b); and e) calculating the percentage of brominated tyrosine in the glatiramer acetate.

The subject invention also provides a process for preparing a pharmaceutical composition containing a mixture of polypeptides which do not all have the same amino acid sequence, where each polypeptide consists essentially of glutamic acid, alanine, tyrosine and lysine, wherein the mixture has a predetermined percentage of brominated tyrosine acceptable for inclusion in a pharmaceutical composition, which comprises obtaining a batch of a mixture of polypeptides having nonuniform amino acid sequences, where each polypeptide consists essentially of glutamic acid, alanine, tyrosine and lysine;

measuring the percentage of brominated tyrosine of the batch by a process comprising a) hydrolyzing the batch to obtain a hydrolyzate;

b) eluting the hydrolyzate through a chromatographic column;

c) measuring the level of bromotyrosine in the hydrolyzate;

d) preparing sample solutions of the amino acid components of the batch and of bromotyrosine;

e) eluting the sample solutions through the column of step b); and f) calculating the percentage of brominated tyrosine in the batch; and including in the pharmaceutical composition a batch only if its percentage of brominated tyrosine so measured is less than 0.3%.

DETAILED DESCRIPTION OF THE INVENTION

The subject invention provides a process for obtaining a mixture of trifluoroacetyl polypeptides which do not all have the same amino acid sequence, where each polypeptide consists essentially of alanine, glutamic acid, tyrosine and trifluoroacetyl lysine, wherein the mixture has a desired average molecular weight and wherein during the process a batch of a mixture of polypeptides, each of which consists essentially of alanine, γ-benzyl glutamate, tyrosine and trifluoroacetyl lysine is deprotected with a solution of hydrobromic acid in acetic acid, the improvement comprising use of a solution of hydrobromic acid in acetic acid, which solution comprises less than 0.5% of free bromine.

In one embodiment, the improvement further comprises use of a solution of hydrobromic acid in acetic acid that comprises less than 1000 ppm of metal ion impurities.

The subject invention further provides a process for obtaining a mixture of trifluoroacetyl polypeptides which do not all have the same amino acid sequence, where each polypeptide consists essentially of alanine, glutamic acid, tyrosine and trifluoroacetyl lysine, wherein the mixture has a desired average molecular weight and wherein during the process a batch of a mixture of polypeptides, each of which consists essentially of alanine, γ-benzyl glutamate, tyrosine and trifluoroacetyl lysine is deprotected with a solution of hydrobromic acid in acetic acid, the improvement comprising use of a solution of hydrobromic acid in acetic acid, which solution comprises less than 1000 ppm of metal ion impurities.

The subject invention yet further provides a process of producing a mixture of trifluoroacetyl polypeptides which do not all have the same amino acid sequence, where each polypeptide consists essentially of alanine, glutamic acid, tyrosine and trifluoroacetyl lysine, wherein the mixture has a desired average molecular weight comprising deprotecting a mixture of polypeptides each consisting essentially of alanine, γ-benzyl glutamate, tyrosine and trifluoroacetyl lysine with a solution of hydrobromic acid in acetic acid, which solution comprises less than 0.5% of free bromine and less than 1000 ppm of metal ion impurities.

In one embodiment, the solution of hydrobromic acid in acetic acid comprises less than 0.1% of free bromine.

In another embodiment, the solution of hydrobromic acid in acetic acid comprises less than 0.05% of free bromine.

In a further embodiment, the solution of hydrobromic acid in acetic acid comprises less than 0.01% of free bromine.

In yet another embodiment, the solution of hydrobromic acid in acetic acid comprises less than 0.001% of free bromine.

In a further embodiment, the solution of hydrobromic acid in acetic acid is free of free bromine.

In another embodiment, the solution of hydrobromic acid in acetic acid comprises less than 1000 ppm of metal ion impurities.

In yet another embodiment, the solution of hydrobromic acid in acetic acid comprises less than 500 ppm of metal ion impurities.

In one embodiment, the solution of hydrobromic acid in acetic acid comprises less than 100 ppm of metal ion impurities.

In another embodiment, the solution of hydrobromic acid in acetic acid comprises less than 30 ppm of metal ion impurities.

In yet another embodiment, the solution of hydrobromic acid in acetic acid comprises less than 20 ppm of metal ion impurities.

In a further embodiment, the solution of hydrobromic acid in acetic acid comprises less than 10 ppm of metal ion impurities.

In another embodiment, the solution of hydrobromic acid in acetic acid is free of metal ion impurities.

In yet another embodiment, the mixture of trifluoroacetyl polypeptides is trifluoroacetyl glatiramer acetate ("TFA GA").

In an embodiment, the hydrobromic acid in acetic acid solution is from 10% to 36% hydrobromic acid in acetic acid. In another embodiment, the hydrobromic acid in acetic acid is from 16% to 33% hydrobromic acid in acetic acid; 18% to 33% hydrobromic acid in acetic acid; 20% to 37% hydrobromic acid in acetic acid; 20% to 33% hydrobromic acid in acetic acid; 22% to 33% hydrobromic acid in acetic acid; 24% to 33% hydrobromic acid in acetic acid; 25% to 35% hydrobromic acid in acetic acid; 26% to 33% hydrobromic acid in acetic acid; 28% to 33% hydrobromic acid in acetic acid; 30% to 34% hydrobromic acid is acetic acid; 30% to 33% hydrobromic acid in acetic acid; or 32% to 33% hydrobromic acid in acetic acid. In a further embodiment, the solution is 33% hydrobromic acid in acetic acid. In another embodiment, the solution is 16% hydrobromic acid in acetic acid.

In another embodiment, the solution is pretreated with a bromine scavenger in order to remove free bromine.

In one embodiment, the bromine scavenger is phenol.

In a further embodiment, the solution is produced in a non-metallic reactor.

In another amendment, the solution is prepared in a glass-lined or polytetrafluoroethylene-lined reactor. Polytetrafluoroethylene is marketed under the trade name TEFLON®. TEFLON® is produced by E I DuPont De Nemours and Company (DUPONT™), Wilmington, Delaware.

In yet another embodiment, the color of the hydrobromic acid in acetic acid solution is less than 2000 APHA.

In a further embodiment, the color of the hydrobromic acid in acetic acid solution is less than 1000 APHA.

In another embodiment, the color of the hydrobromic acid in acetic acid solution is less than 700 APHA.

In yet another embodiment, the color of the hydrobromic acid in acetic acid solution is less than 500 APHA.

The subject invention also provides a trifluoroacetyl product produced by any one of the disclosed processes.

The subject invention further provides a composition comprising the trifluoroacetyl product produced by any one of the disclosed processes, and a carrier.

The subject invention yet further provides a mixture of trifluoroacetyl polypeptides which do not all have the same amino acid sequence, where each polypeptide consists essentially of alanine, glutamic acid, tyrosine and trifluoroacetyl lysine, wherein the mixture has a desired average molecular weight, no more than 0.1% brominated tyrosine and less than 1000 ppm metal ion impurities.

In one embodiment, the mixture of trifluoroacetyl polypeptides has an average molecular weight from 2000 daltons to 40,000 daltons.

In another embodiment, the mixture of trifluoroacetyl polypeptides has an average molecular weight from 4000 daltons to 18,000 daltons.

In a further embodiment, the mixture of trifluoroacetyl polypeptides has an average molecular weight from 4000 daltons to 13,000 daltons.

In another embodiment, the mixture of trifluoroacetyl polypeptides has an average molecular weight from 13,000 daltons to 19,000 daltons.

In yet another embodiment, the mixture of trifluoroacetyl polypeptides has an average molecular weight from 13,500 daltons to 18,500 daltons.

In a further embodiment, the mixture of trifluoroacetyl polypeptides has an average molecular weight of 7,000±2,000 daltons.

In yet a further embodiment, the mixture of trifluoroacetyl polypeptides has an average molecular weight of 7,000 daltons.

In another embodiment, the mixture of trifluoroacetyl polypeptides has an average molecular weight of 14,000 daltons.

In yet another embodiment, the mixture of trifluoroacetyl polypeptides has an average molecular weight from 4,700-11,000 daltons.

In a further embodiment, the mixture of trifluoroacetyl. polypeptides comprises less than 1000 ppm of metal ion impurities.

In yet another embodiment, the mixture of trifluoroacetyl polypeptides comprises less than 500 ppm of metal ion impurities.

In a further embodiment, the mixture of trifluoroacetyl polypeptides comprises less than 100 ppm of metal ion impurities.

In another embodiment, the mixture of trifluoroacetyl polypeptides comprises less than 30 ppm of metal ion impurities.

In a further embodiment, the mixture of trifluoroacetyl polypeptides comprises less than 20 ppm of metal ion impurities.

In another embodiment, the mixture of trifluoroacetyl polypeptides comprises less than 10 ppm of metal ion impurities.

In yet another embodiment, the mixture of trifluoroacetyl polypeptides is free of metal ion impurities.

The subject invention also provides a composition comprising the mixture of trifluoroacetyl polypeptides and a carrier.

The subject invention further provides a process for obtaining a pharmaceutical composition containing a mixture of polypeptides which do not all have the same amino acid sequence, where each polypeptide consists essentially of alanine, glutamic acid, tyrosine and lysine, and wherein the mixture has a desired average molecular weight, which comprises a) polymerizing N-carboxyanhydrides of tyrosine, alanine, γ-benzyl glutamate and N-trifluoroacetyl lysine to form an aqueous mixture of protected polypeptides;

b) deprotecting the protected polypeptides with a solution of hydrobromic acid in acetic acid, which solution comprises less than 0.5% of free bromine and less than 1000 ppm of metal ion impurities, to form an aqueous mixture of trifluoroacetyl polypeptides;

c) reacting the an aqueous mixture of trifluoroacetyl polypeptides with aqueous piperidine to form a solution of aqueous mixture of polypeptides, each of which consists essentially of alanine, glutamic acid, tyrosine and lysine; and d) purifying the aqueous mixture of polypeptides.

In one embodiment, the average mole fraction in the mixture is glutamic acid 0.129-0.159; alanine 0.392-0.462;

tyrosine 0.086-0.100; and lysine 0.300-0.374. In a specific embodiment, the average mole fraction in the mixture of glutamic acid is 0.141, of alanine is 0.427, of tyrosine is 0.093, and of lysine is 0.337.

The subject invention also provides a process of producing glatiramer acetate comprising the steps of:
a) polymerizing N-carboxyanhydrides of tyrosine, alanine, γ-benzyl glutamate and N-trifluoroacetyl lysine to form protected glatiramer acetate;
b) deprotecting protected glatiramer acetate with a solution of hydrobromic acid in acetic acid, the solution comprises less than 0.5% of free bromine and less than 1000 ppm of metal ion impurities, to form trifluoroacetyl glatiramer acetate;
c) reacting trifluoroacetyl glatiramer acetate with aqueous piperidine to form a solution of glatiramer acetate; and
d) purifying the glatiramer acetate.

In one embodiment, the product of the step d) is further subjected to ultrafiltration to remove polypeptide species with molecular weight less than 5000 daltons.

In an embodiment, the hydrobromic acid in acetic acid solution is from 10% to 36% hydrobromic acid in acetic acid. In another embodiment, the hydrobromic acid in acetic acid is from 16% to 33% hydrobromic acid in acetic acid; 18% to 33% hydrobromic acid in acetic acid; 20% to 37% hydrobromic acid in acetic acid; 20% to 33% hydrobromic acid in acetic acid; 22% to 33% hydrobromic acid in acetic acid; 24% to 33% hydrobromic acid in acetic acid; 25% to 35% hydrobromic acid in acetic acid; 26% to 33% hydrobromic acid in acetic acid; 28% to 33% hydrobromic acid in acetic acid; 30% to 34% hydrobromic acid is acetic acid; 30% to 33% hydrobromic acid in acetic acid; or 32% to 33% hydrobromic acid in acetic acid. In a further embodiment, the solution is 33% hydrobromic acid in acetic acid. In another embodiment, the solution is 16% hydrobromic acid in acetic acid.

In another embodiment, the hydrobromic acid in acetic acid solution is pretreated with a bromine scavenger in order to remove free bromine.

In yet another embodiment, the bromine scavenger is phenol.

In a further embodiment, the hydrobromic acid in acetic Acid solution is produced in a non-metallic reactor.

In another amendment, the hydrobromic acid in acetic acid solution is prepared in a glass-lined or TEFLON® container.

In one embodiment, the color of the hydrobromic acid in acetic acid solution is less than 2000 APHA.

In another embodiment, the color of the hydrobromic acid in acetic acid solution is less than 1000 APHA.

In yet another embodiment, the color of the hydrobromic acid in acetic acid solution is less than 700 APHA.

In a further embodiment, the color of the hydrobromic acid in acetic acid solution is less than 500 APHA.

The subject invention further provides method of analyzing the percentage of brominated tyrosine in a sample of glatiramer acetate comprising the steps of:
a) hydrolyzing glatiramer acetate to obtain a hydrolyzate;
b) eluting the hydrolyzate through a chromatographic column;
c) measuring the level of bromotyrosine in the hydrolyzate;
d) preparing sample solutions of the amino acid components of glatiramer acetate and of bromotyrosine;
e) eluting the sample solutions through the column of step b); and
f) calculating the percentage of brominated tyrosine in the glatiramer acetate.

The subject invention also provides a process for preparing a pharmaceutical composition containing a mixture of polypeptides which do not all have the same amino acid sequence, where each polypeptide consists essentially of glutamic acid, alanine, tyrosine and lysine, wherein the mixture has a predetermined percentage of brominated tyrosine acceptable for inclusion in a pharmaceutical composition, which comprises obtaining a batch of a mixture of polypeptides having nonuniform amino acid sequences, where each polypeptide consists essentially of glutamic acid, alanine, tyrosine and lysine;
measuring the percentage of brominated tyrosine of the batch by a process comprising
a) hydrolyzing the batch to obtain a hydrolyzate;
b) eluting the hydrolyzate through a chromatographic column;
c) measuring the level of bromotyrosine in the hydrolyzate;
d) preparing sample solutions of the amino acid components of the batch and of bromotyrosine;
e) eluting the sample solutions through the column of step b); and
f) calculating the percentage of brominated tyrosine in the batch; and
including in the pharmaceutical composition a batch only if its percentage of brominated tyrosine so measured is less than 0.3%.

In one embodiment, the batch is acceptable for inclusion in the pharmaceutical composition only if its percentage of brominated tyrosine so measured is less than 0.2%.

In another embodiment, the batch is acceptable for inclusion in the pharmaceutical composition only if its percentage of brominated tyrosine so measured is less than 0.1%.

In a further embodiment, the mixture of polypeptides is glatiramer acetate ("GA").

Terms

The term "average molecular weight" as used in this application means the molecular weight of the species of polypeptides present in the mixture in the highest relative proportion (i.e. the peak maximum) when the mixture is subjected to separation by molecular weight on an HPLC gel permeation column. This value can be obtained in several ways, e.g. from the retention time on a calibrated column; or from a correlation between the location of the peak and the location of the cochromatographed copolymer markers of defined sequence and molecular weight. Other methods of determining an average molecular weight such as by light scattering may be employed and will correspond substantially to the value obtained from the peak maximum.

A polypeptide mixture according to this invention as exemplified is the acetate salt of synthetic polypeptides prepared by chemically reacting four activated amino acid derivatives (two of them L-Glutamic acid and L-lysine protected): L-Glutamic acid (L-Glu), L-alanine (L-Ala), L-tyrosine (L-Tyr) and L-lysine (L-Lys) (two of them protected i.e. 5Bz-Glutamate derivative and 6N-TFA-Lysine derivative) in a specified ratio. The term "mixture" as used in this document generally refers to in the "mixture of polypeptides of the invention" comprising L-glutamic acid, L-alanine, L-tyrosine, and L-lysine, and both terms are meant to include residual impurities from the manufacturing process.

The molar fraction range of each amino acid residue is: L-Glu 0.129-0.153, L-Ala 0.392-0.462, L-Tyr 0.086-0.100 and L-Lys 0.300-0.374.

Because no reaction goes to completion 100% and although practically all impurities are eliminated, small amounts can remain. Such impurities may be of the following three types:

Structure-related substances, which are protected amino acid residues such as 5-BZ-L-glutamyl and/or N6-TFA-L-Lysyl residues, originating from incomplete removal of the protecting groups. In addition, the polypeptide mixture of the invention molecules may contain brominated L-tyrosyl residues, formed during production due to the presence of free bromine in the HBr/acetic acid reagent.

The molecular structures of the identified structure-related impurities can be derived from the participating monomers i.e. starting materials.

These identified impurities are quantified (after chemical conversion) by comparison to the specific Reference Standards, which are either derivatives or part of the impurities themselves:

Residual trifluoroacetyl compounds (expressed as fluoride)

Residual benzylated glutamyl residues (expressed as benzyl bromide)

Residual brominated tyrosyl residues (expressed as bromotyrosine)

Unidentified related substances (determined by RP-HPLC): these are small molecular size polypeptides of the same origin with similar structures. These substances probably have similar response factors and the concentration (%) of each impurity can be calculated as % peak area relative to the the polypeptide mixture of the invention peak area.

The characterization of the impurities is based on their relative chromatography retention time (RRT) relative to the L-Tryptophan standard.

Residual solvents and inorganic impurities covered in the specification such as the residual solvent 1,4 dioxane, residual piperidine and heavy metals.

Discussion

Free Bromine

In the manufacturing process for mixtures of polypeptides, such as GA, 33% hydrobromic acid in acetic acid is used to deprotect protected GA. For example, during the development of the production process for GA it was found that some of the tyrosine residues in trifluoroacetyl GA (TFA GA) and in GA were brominated. This impurity was isolated and identified using an analytical procedure that is described in detail in the examples. The tyrosine residue was found to react with bromine to form a mono-bromotyrosine moiety comprising either 2-bromotyrosine or 3-bromotyrosine.

After much investigation the inventors discovered that the brominated tyrosine impurity was introduced into the GA through free bromine in HBr/acetic acid. The free bromine was present in 33% HBr/acetic acid bought from a supplier and used in the production process.

Measures were taken in order to decrease the level of free bromine in 33% HBr/acetic acid. For example, pre-treatment of HBr/acetic acid with a bromine scavenger was effective in removing some of the free bromine from the HBr/acetic acid solution.

One of the bromine scavengers used in the HBr purification process was phenol. In addition to phenol, other reducing agents, such as sodium bisulfite, may be used. Phenol was chosen as a bromine scavenger because it and its reaction product with bromine (bromophenols) are both essentially non-reactive with protected polypeptides, such as protected GA, TFA polypeptides, such as TFA GA and polypeptides, such as GA, and they are easy to remove from the solution of GA during the purification process. Similarly, any bromine scavenging agent may be used provided that it, and its reaction product with bromine, are not reactive with protected polypeptides, such as protected GA, TFA polypeptides, such as TFA GA and polypeptides, such as GA, and it is easily removable during the final purification process.

Metal Impurities

GA is marketed in two pharmaceutical dosage forms, lyophilized powder and pre-filled syringes. The syringe, marketed under the trade name COPAXONE® Injection, generally contained clear solution. The storage instructions were to keep the syringe refrigerated. However, red color in aqueous solutions of COPAXONE® pre-filled solutions was detected. The source of the color in the solutions was unknown.

The color appeared when the solutions were kept at room temperature for 12 to 24 hours.

It was determined that production of HBr in metal apparatus led to trace metallic ion impurities in the HBr. When HBr was later mixed with protected GA, the metallic ion impurities in the HBr were chelated by TFA GA and GA. These TFA GA and GA/metal complexes contributed to the coloration.

As a result, another measure taken to ensure purity, e.g., in the GA product, was the use of a non-metal reactor for the production of 33% HBr/acetic acid solution. The reactor used for the production of HBr/acetic acid solution was glass lined in order to prevent the formation of impurities which could later affect the purity of, e.g., the GA. In order to prevent contact of HBr solution with metal, parts of the piping used were TEFLON®-lined. Similarly, other types of non-reactive, acid resistant non-metal apparatus can be used to prevent the formation of trace metal ions in the HBr/acetic acid solution. The use of a non-metal apparatus for the production of HBr/acetic acid solution was successful in eliminating the red color from the GA. When the non-metal apparatus was used for the production of the HBr/acetic acid solution, the result was that the solution was essentially free of metal ions and the red GA was not formed.

In addition, the color of every batch of HBr/acetic acid is measured to determine level of impurities before being used to deprotect protected GA. It was found that levels of metal ion impurity in HBr solution could be determined by visual analysis. HBr solution with a color below 2000 APHA was shown to produce glatiramer acetate without red color.

The invention will be exemplified but not limited by the following examples.

Experimental Details

EXAMPLE 1

Influence of Bromine Concentration in HBR Acetic Acid on Bromominated Tyrosine Moiety in TFA GA and in GA In order to determine the effect of free bromine in hydrobromic acid/acetic acid on the level of brominated tyrosine moiety impurity in TFA-GA and GA, hydrobromic acid in acetic acid was contaminated with various amounts of bromine. In the experiment, HBr which was not pretreated with bromine scavenger was used in the manufacturing process. Various levels of bromine impurity (measured as percentage of HBr/Acetic acid solution) were added. The level of brominated tyrosine moiety impurity in TFA GA and in GA was measured by hydrolyzing TFA GA and GA to its amino acid components, and then using HPLC to determine the amount of bromotyrosine in relation to the TFA GA and GA.

Procedure

Preparation of Standard Solutions

Standard solutions containing 2 µg/mL Bromotyrosine were prepared using distilled water. Amino acid standard stock solution was prepared using the following amino acids:

| | |
|---|---|
| L-Glu | About 100 mg |
| L-Ala | About 130 mg |
| L-Tyr | About 75 mg |
| L-Lys HCl | About 200 mg |

The amino acids were dissolved in water. A few drops of 5 N NaOH were added and water was added to a final volume of 25 mL.

Hydrolysis 10 mg of glatiramer acetate and 10 mg of TFA GA were each independently weighed into 5 mL hydrolysis vials. A negative control vial was prepared by adding 0.5 mL of the amino acid standard stock solution to a 5 mL hydrolysis vial. 0.5 mL of water and 0.5 mL of concentrated HCl containing 1% of phenol were added to each of the vials. The vials were heated to 110° C for 24 hours, under $N_2$ atmosphere. The samples were then cooled to room temperature. Each of the hydrolyzates were transferred to 5 mL volumetric flasks and filled to volume with distilled water.

Chromotography

The bromotyrosine standard, and each of the hydrolyzates, were independently eluted through an HPLC column using an eluent of acetonitrile:water:acetic acid in a ratio of 4:95:1. The column was equipped with an UV detector and data recording system. The amino acid standard is used as a negative control to determine which peak in the glatiramer acetate hydrolyzate corresponds to bromotyrosine.

Data Analysis

The percentage of brominated tyrosine moiety in each TFA GA and GA sample was calculated as follows:

P=purity of bromotyrosine standard (in percent)

As=Area of bromotyrosine standard peak

Ap=Area of bromotyrosine peak in each sample

Cs=Concentration of bromotyrosine standard (μg/mL)

Cp=Concentration of glatiramer acetate (or of TFA GA)

$$\% \text{ Brominated tyrosine} = p * \frac{Ap}{As} * \frac{Cs}{Cp}$$

Table 1 shows the effect of free Bromine on the level of brominated tyrosine moiety in TFA Glatiramer Acetate and in Glatiramer Acetate

TABLE 1

Effect Of Free Bromine On The Level Of Brominated Tyrosine Moiety

| | Brominated tyrosine (%) | |
|---|---|---|
| Bromine (%) | TFA Glatiramer | Glatiramer Acetate |
| No added Bromine | 0.1 | 0.2 |
| 0.5 | 0.7 | 1.2 |
| 1 | 1.2 | 2.2 |
| 5 | 4 | No Data |

Results

From the above example it can be seen that contamination of HBr with bromine leads to higher levels of brominated tyrosine moiety in TFA GA and in GA, relative to the standard reaction in which no bromine was added. When no bromine was added, since the HBr was not treated with a bromine scavenger, some free bromine was still available and brominated tyrosine moiety contamination of GA and TFA GA was still evident.

In order to produce GA with brominated tyrosine moiety impurity at a level of less than 0.2%, the level of free Bromine in HBr must be lowered by the addition of a bromine scavenger.

EXAMPLE 2

Production of 33% HBR in Acetic Acid Solution

The glass-lined reactor is rinsed with acetic acid, then emptied. 1013 kg of acetic acid is added into the reactor. The acetic acid is maintained at a temperature of 10-20° C. 522 kg of HBr gas is introduced into the reactor while mixing the solution. After the gas is introduced, the solution is mixed for an additional 30 minutes. The solution is tested to determine if HBr content is 33%.

EXAMPLE 3

Purification of HBR/Acetic Acid Solution using Phenol as a Bromine Scavenger

A solution of 33% HBr in acetic acid was poured into a glass-lined reactor. Phenol was weighed and added to the HBr solution in a weight ratio of 1 to 100. The solution was then stirred for 12 to 24 hours. The purified HBr solution is then added to protected glatiramer acetate. The reaction of the HBr with protected GA forms TFA GA. The TFA GA is reacted with piperidine to form GA.

EXAMPLE 4

Levels of Brominated Tyrosine in Various Batches

The level of Brominated tyrosine moiety in various batches of glatiramer acetate was measured using the method described in example 1.

| Method of Production | Batch Number of GA | Brominated tyrosine moiety concentration |
|---|---|---|
| OLD METHOD | A | 0.15 |
| | B | 0.19 |
| | C | 0.14 |
| | D | 0.15 |
| | E | 0.32 |
| NEW METHOD | X | None detectable |
| | Y | None detectable |
| | Z | None detectable |

Results

The HBr produced using the new method, as described in example 2 and treated with phenol as in example 3, was free of Bromine and metallic impurities. Therefore the glatiramer acetate which was produced was substantially free of brominated tyrosine moiety.

The HBr which was bought from external suppliers (old method) had impurities, and therefore the glatiramer acetate produced using it also had brominated tyrosine moiety impurities, even though phenol was used as a tyrosine scavenger.

EXAMPLE 5

Color Determination

The color of the HBr/acetic acid solution was determined using standard visual color determination techniques.

The American Public Health Association (APHA) color index is a single number yellowness index where each API-IA unit is based on a dilution of the 500 ppm stock solution of platinum-cobalt (PtCo). (HunterLab, APHA Background, Applications Note, Insight on Color Nov. 16-30, 1996, Vol. 8, No. 16. available at hunterlab.com/appnotes/an11$_{13}$ 96br2 .pdf.) The APHA measurement is determined by visual comparison of the solution with PtCo standards that contain controlled amounts of potassium chloroplatinate and cobaltous chloride. Each number unit is the equivalent of 1 mg of platinum per liter of solution (ppm). The standards and corresponding measurements are designated according to their ppm measurement, i.e. the No. 20 APHA standard contains 20 ppm of platinum. American Chemical Society, General Directions and Procedures: Measurement of Physical Properties available at pubs.acs .org/reagent$_{13}$ demo/sec$_{13}$ b002 .html.), distille water has an APHA value of 0, and the stock solution has an APHA value of 500 ppm. (HunterLab, APHA Background, Applications Note, Insight on Color, Nov. 16-30, 1996, Vol. 8, No. 16. available at hunterlab. com/appnotes/an11$_{13}$ 96br2 .pdf.) The APHA measurement may be made by various instruments well known in the art.

APHA color standard "500" and APHA color standard "1000" were prepared. APHA color standard "500" was prepared by dissolving 1.246 g Potassium Chloroplatinate, $K_2PtCl_6$ (equivalent to 50 mg metallic Platinum) and 1.00 g crystallized Cobaltous Chloride, $CoCl_2$-$6H_2O$ (equivalent to about 250 mg metallic Cobalt) in distilled water with 100 ml concentrated HCl and was diluted to 1000 mL with distilled water.

APHA color standard "1000" was prepared by dissolving 2.492 g Potassium Chloroplatinate $K_2PtCl_6$ and 2.00 g crystallized Cobaltous Chloride $CoCl_2$-$6H_2O$ in distilled water with 200 mL concentrated HCl and was diluted to 1000 mL with distilled water.

The following batches were produced using non-metal apparatus as described previously. These samples were color-tested visually against the color standards by viewing 100 mL Nessler tubes vertically against a white background.

| Batch Number | Color (APHA) |
|---|---|
| M | <500 |
| N | <500 |
| P | 700 |
| Q | 350 |
| R | <300 |

The color of these batches of HBr/acetic acid indicated that they were essentially free of bromine and metal ion impurities. Because the color was less than 2000 APHA, these batches were considered essentially free of metal ion impurities.

What is claimed is:

1. A process for obtaining a pharmaceutical composition containing a mixture of polypeptides which do not all have the same amino acid sequence, where each polypeptide consists essentially of alanine, glutamic acid, tyrosine and lysine, and wherein the mixture has a desired average molecular weight, which comprises
    i) treating a solution of hydrobromic acid in acetic acid with a bromine scavenger so as to prepare a treated hydrobromic acid in acetic acid solution, and
    ii) a) polymerizing N-carboxyanhydrides of tyrosine, alanine, y-benzyl glutamate and N-trifluoroacetyl lysine to form a mixture of protected polypeptides;
    b) deprotecting the protected polypeptides with the treated hydrobromic acid in acetic acid solution prepared in part i), to form a mixture of trifluoroacetyl polypeptides;
    c) reacting the mixture of trifluoroacetyl polypeptides with aqueous piperidine to form a solution of aqueous mixture of polypeptides, each of which consists essentially of alanine, glutamic acid, tyrosine and lysine; and
    d) purifying the mixture of polypeptides.

2. The process of claim 1, wherein in the mixture the molar fraction of alanine is 0.427, of glutamic acid is 0.141, of lysine is 0.337 and of tyrosine is 0.093.

3. A process of producing glatiramer acetate comprising the steps of:
    i) treating a solution of hydrobromic acid in acetic acid with a bromine scavenger so as to prepare a treated hydrobromic acid in acetic acid solution, and
    ii) a) polymerizing N-carboxyanhydrides of tyrosine, alanine, γ-benzyl glutamate and N-trifluoroacetyl lysine to form protected polypeptides;
    b) deprotecting protected polypeptides with the treated hydrobromic acid in acetic acid solution prepared in part i) to form trifluoroacetyl glatiramer acetate;
    c) reacting trifluoroacetyl glatiramer acetate with aqueous piperidine to form a solution of glatiramer acetate; and
    d) purifying the glatiramer acetate.

4. The process of claim 3, further comprising subjecting the product of the step d) to ultrafiltration.

5. The process of claim 4, wherein the hydrobromic acid in acetic acid solution is 10%-36% hydrobromic acid in acetic acid.

6. The process of claim 5, wherein the hydrobromic acid in acetic acid solution is 33% hydrobromic acid in acetic acid.

7. The process of claim 3, wherein the bromine scavenger is phenol.

8. The process of claim 3, wherein in part
    i) the hydrobromic acid in acetic acid solution is produced in a non-metallic reactor.

9. The process of claim 3, wherein in part
    i) the hydrobromic acid in acetic acid solution is prepared in a glass-lined or polytetrafluoroethylene-lined reactor.

10. The process of claim 3, wherein the color of the hydrobromic acid in acetic acid solution is less than 2000 APHA.

11. The process of claim 10, wherein the color of the hydrobromic acid in acetic acid solution is less than 1000 APHA.

12. The process of claim 11, wherein the color of the hydrobromic acid in acetic acid solution is less than 700 APHA.

13. The process of claim 12, wherein the color of the hydrobromic acid in acetic acid solution is less than 500 APHA.

14. The process of claim 3, wherein the hydrobromic acid in acetic acid solution is 10%-36% hydrobromic acid in acetic acid.

15. The process of claim 3, where in the hydrobromic acid in acetic acid solution is 33% hydrobromic acid in acetic acid.

16. In a process for obtaining a pharmaceutical composition containing a mixture of polypeptides which do not all have the same amino acid sequence, where each polypeptide consists essentially of alanine, glutamic acid, tyrosine and lysine, and wherein the mixture has a desired average molecular weight, which process comprises:
   a) polymerizing N-carboxyanhydrides of tyrosine, alanine, γ-benzyl glutamate and N-trifluoroacetyl lysine to form a mixture of protected polypeptides;
   b) deprotecting the protected polypeptides with a solution of hydrobromic acid in acetic acid, to form a mixture of trifluoroacetyl polypeptides;
   c) reacting the mixture of trifluoroacetyl polypeptides with aqueous piperidine to form a solution of aqueous mixture of polypeptides, each of which consists essentially of alanine, glutamic acid, tyrosine and lysine; and
   d) purifying the mixture of polypeptides,
      the improvement comprising:
      pretreating the solution of hydrobromic acid in acetic acid with a bromine scavenger prior to use of the solution in step b) for deprotecting the protected polypeptides.

17. In a process of producing glatiramer acetate comprising the steps of:
   a) polymerizing N-carboxyanhydrides of tyrosine, alanine, γ-benzyl glutamate and N-trifluoroacetyl lysine to form a mixture of protected polypeptides;
   b) deprotecting the protected polypeptides with a solution of hydrobromic acid in acetic acid, to form trifluoroacetyl glatiramer acetate;
   c) reacting the trifluoroacetyl glatiramer acetate with aqueous piperidine to form a solution of glatiramer aceate; and
   d) purifying the glatiramer acetate,
      the improvement comprising:
      pretreating the solution of hydrobromic acid in acetic acid with a bromine scavenger prior to use of the solution in step b) for deprotecting the protected polypeptides.

18. The process of claim 16, wherein the hydrobromic acid in acetic acid solution is from 10% to 36% hydrobromic acid in acetic acid.

19. The process of claim 16, wherein the hydrobromic acid in acetic acid solution is 33% hydrobromic acid in acetic acid.

20. The process of claim 17, wherein the hydrobromic acid in acetic acid solution is from 10% to 36% hydrobromic acid in acetic acid.

21. The process of claim 17, wherein the hydrobromic acid in acetic acid solution is 33% hydrobromic acid in acetic acid.

\* \* \* \* \*